United States Patent [19]

Meezan et al.

[11] Patent Number: 5,384,128
[45] Date of Patent: Jan. 24, 1995

[54] METHOD OF AND COMPOUNDS FOR TREATMENT FOR CYSTIC FIBROSIS

[75] Inventors: Elias Meezan; Rongxiang Wang, both of Birmingham, Ala.

[73] Assignee: University of Alabama Research Foundation, Birmingham, Ala.

[21] Appl. No.: 25,627

[22] Filed: Mar. 2, 1993

[51] Int. Cl.⁶ .................... A61K 37/22; A61K 9/70; A61F 9/02; A61L 9/04

[52] U.S. Cl. ...................... 424/450; 424/45; 424/436; 424/449; 424/451; 424/464; 436/829; 514/937; 514/962; 514/963

[58] Field of Search .......... 424/45, 449, 450, 436, 424/450, 451, 464; 264/436, 4, 4.1; 436/829; 514/937, 962, 963

[56] References Cited

U.S. PATENT DOCUMENTS 4,826,679  5/1989  Roy ........................ 514/851

OTHER PUBLICATIONS

Physicians' Desk Reference, 47th Ed., *Medical Economics Data*, Montvale, N.J., pp.782–785 (1993).

Eduardo F. Tizzano et al., "Cystic Fibrosis: Beyond the Gene to Therapy," *The Journal of Pediatrics*, 120(3):337–349 (Mar. 1992).

Richard C. Boucher, "Drug Therapy in the 1990s: What Can We Expect for Cystic Fibrosis?" *Drugs*, 43(4):431–439 (1992).

Michael R. Knowles et al., "A Pilot Study of Aerosolized Amiloride for the Treatment of Lung Disease in Cystic Fibrosis," *N. Eng. J. Med.*, 322:1189–1194 (1990).

Igor M. Gladstone et al., "Effect of Artificial Surfactant on Pulmonary Function in Preterm and Full-Term Lambs," *J. Appl. Physiol.*, 69:465–472 (1990).

Nikolaus Weber et al., "Metabolism of Orally Administered Alky β-Glycosides in the Mouse," *J. Nutr.*, 114:247–254 (1984).

*Primary Examiner*—Thurman K. Page
*Assistant Examiner*—Carlos Azpuru
*Attorney, Agent, or Firm*—Needle & Rosenberg

[57] ABSTRACT

This invention provides a method and compositions for increasing the permeability of epithelial cells to a chloride ion in a subject comprising administering a permeability enhancing amount of a composition comprising a nontoxic, nonionic surfactant having (1) a critical micelle concentration of less than about 10 mM and a hydrophile-lipophile balance number of from about 10 to 20 and (2) a suitable hydrophobic organic group joined by a linkage to a suitable hydrophilic polyol.

22 Claims, 10 Drawing Sheets

Rat Aortic Smooth Muscle Cells

METHOD OF AND COMPOUNDS FOR TREATMENT FOR CYSTIC FIBROSIS

BACKGROUND OF THE INVENTION

1. Field of the Invention

The instant invention relates to a method of increasing the permeability of epithelial cell chloride ($Cl^-$) channels and a method of treating cystic fibrosis. In particular, the method comprises administering a nontoxic, nonionic surfactant having (1) a critical micelle concentration of less than about 10 mM and a hydrophile-lipophile balance number of from about 10 to 20, and (2) a hydrophobic organic group and a hydrophilic polyol. Additionally provided are compositions for treating cystic fibrosis and for increasing permeability of epithelial cells to chloride.

2. Background Art

Cystic fibrosis is the most common autosomal recessive disease in Caucasians. The disease is a complex disorder mainly affecting organs with epithelial cell linings, including the airways, pancreas, intestine, sweat glands and male genital tract. The primary defect in CF is a relative impermeability of the epithelial cells of these organs to chloride ion. The lung and the GI tract are the predominant organ systems affected in this disease and the pathology is characterized by blocking of the respiratory and GI tract with viscous mucus. The $Cl^-$ impermeability in affected tissues is due to mutations in a specific chloride channel, the cystic fibrosis transmembrane conductance regulator protein (CFTR), which prevents normal passage of $Cl^-$ ions through the cell membrane (Welsh et al., *Neuron*, 8:821–829 (1992)). There is no effective treatment for the disease, and therapeutic research is focused on gene therapy and/or activating the defective or other $Cl^-$ channels in the cell membrane to normalize $Cl^-$ permeability (Tizzano et al., *J. Pediat.*, 120:337–349 (1992)). Damage to the lung due to mucus blockage, frequent bacterial infections and inflammation is the primary cause of morbidity and mortality in CF patients and although maintenance therapy has improved the quality of patients' lives, the median age at death is around 30 years.

A major advance in our understanding of the metabolic basis for cystic fibrosis and in the development of therapies to treat the disease came with the discovery and characterization of the cystic fibrosis transmembrane conductance regulator (CFTR), the specific chloride channel which is defective in CF (see Welsh et al., for review). All cases of CF are due to mutations in the CFTR protein, the most common being a deletion of the phenylalanine residue at position 508 of the protein ($\Delta$F508). A model cell to study the structure and function of native CFTR is the T84 cell line derived from a colonic adenocarcinoma which expresses high levels of the CFTR chloride channel protein (Cohn et al., *Proc. Natl. Acad. Sci. USA*, 89:2340–2344 (1992)).

A breakthrough in the development of a continuous cell line expressing the major mutation in CFTR found in CF was the establishment of a pancreatic adenocarcinoma cell line from a patient with cystic fibrosis (Schoumacher et al., *Proc. Natl. Acad. Sci. USA*, 87:4012–4016 (1990)). This cell line, designated CFPAC-1, is homozygous for the $\Delta$F508 mutation and expresses the characteristic $Cl^-$ channel defect in CF, the inability of the channel to be activated by forskolin, cAMP or phosphodiesterase inhibitors, all agents which activate CFTR in T84 cells. The $Cl^-$ channel defect in this cell line could be corrected by introducing functional CFTR cDNA into the cell by transduction with a CFTR expressing retrovirus (Drumm et al., *Cell*, 62:1227–1233 (1990)).

The efflux of $^{125}I^-$ has been shown to be a simple assay for agonist-regulated $Cl^-$ channels in salt secreting epithelial cells (Venglarik et al., *Am. J. Physiol.*, 259:C358–C364 (1990)). The activation of the defective and/or alternative functioning chloride channels in cystic fibrosis epithelial cells in order to normalize their permeability to chloride is one of the primary therapeutic goals of the treatment of cystic fibrosis and has not yet been accomplished (Boat, T. F., Welsh, M. J. and Beaudet, A. L., "Cystic Fibrosis" in *The Metabolic Basis of Inherited Disease*, pp. 2649–2680 (Striver, C. R., Beaudet, A. L., Sly, W. S. and Valle, D. eds.) McGraw-Hill, New York (1989)). Thus, there exists an urgent need for a treatment that increases the permeability of epithelial cells to chloride and thereby can be used to treat cystic fibrosis. Such a treatment would be most beneficial if it were nontoxic and nonirritating to the epithelial cell linings, yet allowed the restoration of the proper chloride equilibrium of the cells, as well as the clearing of existing mucus. The present invention satisfies this need by providing methods and compounds which can therapeutically relieve both the cause of the manifestations of cystic fibrosis, as well as the manifestations themselves.

SUMMARY OF THE INVENTION

The present invention relates to a method of increasing the permeability of epithelial cells to a chloride ion in a subject comprising administering a permeability enhancing amount of a composition comprising a nontoxic, nonionic surfactant having (1) a critical micelle concentration of less than about 10 mM and a hydrophile-lipophile balance number of from about 10 to 20 and (2) a suitable hydrophobic organic group joined by a linkage to a suitable hydrophilic polyol.

The invention also relates to a method of treating cystic fibrosis comprising administering an epithelial cell chloride permeability enhancing amount of a composition comprising a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophilic polyol.

The invention also relates to a composition for treating cystic fibrosis comprising (1) a nontoxic, nonionic surfactant having (a) a critical micelle concentration of less than about 10 mM and a hydrophile-lipophile balance number of from 10 to 20, and (b) a suitable hydrophobic organic group joined by a linkage to a suitable hydrophilic polyol, and (2) an agent selected from the group consisting of amiloride, human DNase I, cystic fibrosis transmembrane conductance regulator protein or a biologically active portion thereof, nucleic acid encoding functional cystic fibrosis transmembrane conductance regulator protein, a cyclic AMP agonist, a calcium ion agonist, and a pancreatic enzyme supplement.

Accordingly, it is an object of the instant invention to provide a method of increasing the permeability of epithelial cells to a chloride ion in a subject comprising administering a permeability enhancing amount of a composition comprising a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophilic polyol.

It is a further object of the instant invention to provide a method of treating cystic fibrosis comprising administering an epithelial cell chloride permeability enhancing amount of a composition comprising a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophilic polyol.

Another object of the instant invention is to provide a composition for treating cystic fibrosis comprising (1) a nontoxic, nonionic surfactant having (1) a critical micelle concentration of less than about 10 mM and a hydrophile-lipophile balance number of from about 10 to 20, and (b) a suitable hydrophobic organic group joined by a linkage to a suitable hydrophilic polyol, and (2) an agent selected from the group consisting of amiloride, human DNase I, cystic fibrosis transmembrane conductance regulator protein or a biologically active portion thereof, nucleic acid encoding functional cystic fibrosis transmembrane conductance regulator protein, a cyclic AMP agonist, a calcium ion agonist, and a pancreatic enzyme supplement.

DETAILED DESCRIPTION OF THE INVENTION

Figure 1:
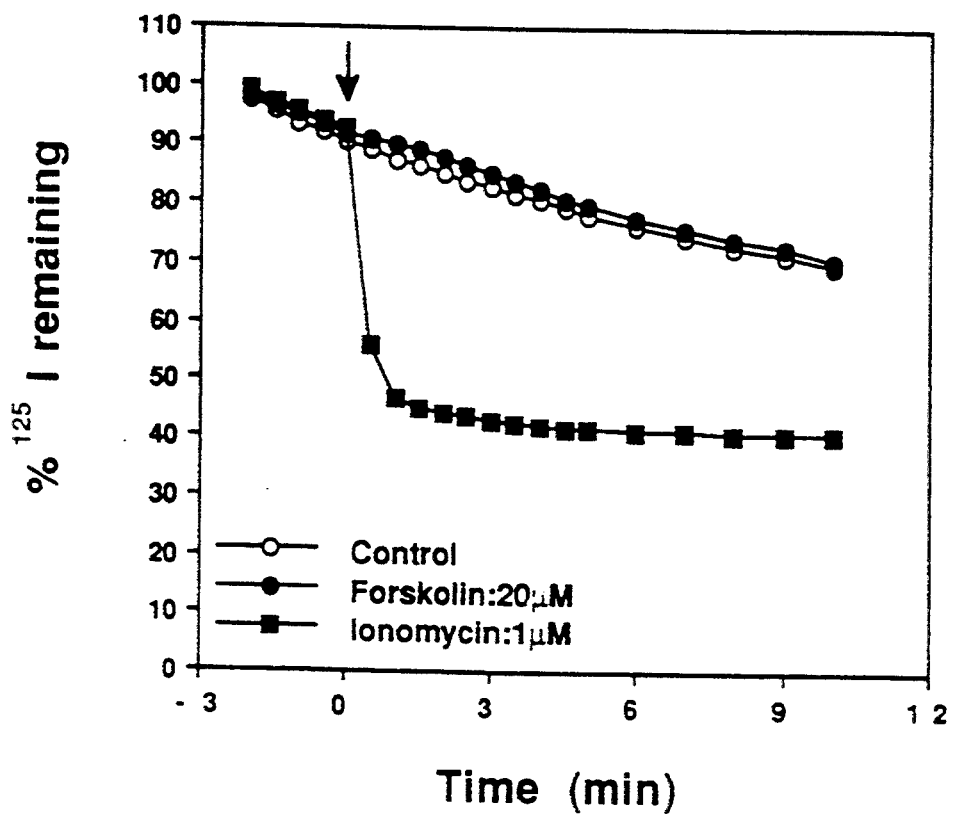

The present invention may be understood more readily by reference to the following detailed description of specific embodiments and the Examples and Figures included therein.

As used in the claims, "a" means one or more.

As used herein, "surfactant," a term well known to those skilled in the art, refers generally to compounds that exhibit properties such as foaming, the appearance of micelles, and interfacial or surface activity in solution; "nonionic surfactant" refers to a surfactant with no charged moieties. Some nonionic detergents, however, are converted to cationic detergents by protonation at acidic pH. In those cases, the cationic species has a different critical micelle concentration than the nonionic species.

As used herein, "a permeability enhancing amount" of a composition is that amount that causes the epithelial cell membrane to allow the passage of chloride ions through the cell membrane chloride channels. The efflux of $^{125}I$ is a simple in vitro assay for agonist-regulated $Cl^-$ channels in salt secreting epithelial cells.

As used herein, "critical micelle concentration" is defined as the limit of surfactant concentration in aqueous solution under physiological conditions (i.e., approximately 0.9% NaCl) above which micelles are formed. CMC can be determined by many methods, including surface tension, classical light scattering and solubilization (Mukerjee, P. and Mysels, K. J., NSRDS-NBS 36 (1970)). The resulting CMC can vary with the method used. Furthermore, the CMC of some nonionic surfactants are slightly lowered with added salt. The formula for micelle concentration in moles per liter is:

$$[micelles] = \frac{[C_s] - CMC}{N},$$

where $[C_s]$ is the bulk molar concentration of surfactant, N is the mean aggregation number, and CMC is the critical micelle concentration in moles per liter (Neugebauer, J., *A Guide to the Properties and Uses of Detergents in Biology and Biochemistry*, Calbiochem Corporation (1988)).

As used herein, a "suitable" group means one that, when a part of a particular surfactant molecule, will render the surfactant able to fulfill the limiting characteristics of the invention, i.e., that the surfactant be nontoxic and nonionic, that it have a hydrophile-lipophile balance number between about 10 and 20 and that it have a critical micelle concentration of less than about 10 mM. Suitable compounds can be determined using the methods set forth in the examples.

Also as used herein, "hydrophile-lipophile balance number" (HLB) is a characteristic of individual detergents that can be either calculated or determined empirically, as previously described (Schick, M. J. *Nonionic Surfactants*, p. 607 (NY: Marcel Dekker, Inc. (1967)). HLB can be calculated by the formula: 20×MW hydrophilic component/(MW hydrophobic component+MW hydrophilic component), where MW=molecular weight (Rosen, M. J., *Surfactants and Interfacial Phenomena*, pp. 242–245, John Wiley, New York (1978)). The HLB is a direct expression of the hydrophilic character of the surfactant, i.e., the larger the HLB, the more hydrophilic the compound.

As used herein, "polyol" is a polyhydroxy compound which comprises the hydrophilic moiety of a nonionic surfactant.

As used herein, "saccharide" is inclusive of monosaccharides, oligosaccharides or polysaccharides in straight chain or ring forms.

As used herein, "cyclic AMP agonist" refers to any compound that increases intracellular cyclic AMP such that cAMP-mediated $Cl^-$ channels in cell membranes are thereby opened. Examples include forskolin and isoproterenol (Sigma Chemical Co., St. Louis, Mo.).

Also used herein, "calcium ion agonist" refers to an agent that elevates intracellular levels of $Ca^{++}$, thereby potentially stimulating $Ca^{++}$-activatable $Cl^-$ channels in cells. Such compounds include ionomycin (Sigma Chemical Co.; U.S. Pat. No. 3,873,693), A23187 (Calbiochem, San Diego, Calif.; U.S. Pat. No. 3,923,823), carbachol (Sigma Chemical Co.), bradykinin, (Boucher et al., *J. Clin. Invest.*, 84:1424–1431 (1989)) duramycin (Cloutier et al., *Abstract Pediatric Pulmonology Suppl.*, 2:99 (1988)), and thapsigargin (Kwan et al., *Am. J. Physiology*, 258:C1006–C1015 (1990)).

As used herein, "sodium channel blocker" refers to a compound capable of blocking the sodium channel in epithelial cells, thus interfering with sodium absorption into the cells. Some examples include amiloride (Glaxo, Inc. (aerosol formulation of amiloride HCl ); Merck Sharpe and Dohme (tablet form of amiloride HCl)) and triamterene (Smith, Kline and French; Lederle).

"Functional cystic fibrosis transmembrane conductance regulator protein," as used herein, refers to the CFTR protein having the proper characteristics to allow it to function properly, i.e. to correct the $Cl^-$ channel defect in cells lacking or deficient in CFTR protein or cells having defective CFTR protein. The phrase "or a biologically active portion thereof" means any portion of the CFTR protein that confers the $Cl^-$ channel activating effect to cells (see, e.g., Welsh et al., *Neuron*, 8:821–829 (1992)). Biologically active portions can be determined utilizing standard protein alteration and activity screening methods.

As used herein, "respiratory distress syndrome" refers to either adult or neonatal respiratory distress syndrome, and "a syndrome relieving amount" means that amount capable of relieving any of the symptoms of respiratory distress syndrome such as mucus plugs adhered along the surface of the lumen of the lung.

As used herein, "pancreatic enzyme supplement" refers to any composition comprising pancreatic enzymes, e.g., lipase, protease and amylase, in any combination thereof. Enzymes can be extracted from pancreatic tissue as known to those skilled in the art. Preparations also can be obtained commercially, e.g., enteric coated tablets (Eli Lilly & Co.) and enteric coated microspheres (Reid-Rowell, Marietta, Ga.).

Surfactants useful for increasing permeability of cells include those that contain a hydrophobic organic group linked to a hydrophilic polyol. A balance of hydrophobicity and hydrophilicity contributes to the ability to increase permeability. A preferred balance of hydrophobicity and hydrophilicity is found in surfactants having an HLB of from about 10 to 20. A more preferred balance is between about 12 to 14. The composition can be chosen from existing compounds, or one can synthesize a preferred compound.

Useful surfactants also have a critical micelle concentration (CMC) of less than about 10 mM. More preferable surfactants have a CMC of less than 1 mM.

Any composition chosen should be of low or non-toxicity to the cell. Toxicity for any given compound may vary with the concentration of compound used. It is also beneficial if the compound chosen is metabolized or eliminated by the body and if this metabolism or elimination is done in a manner that will not be harmfully toxic.

The hydrophobic organic group can be, for example, an alkyl chain, an aralkyl group, an aryl group, or asteroid group. An alkyl chain can be chosen of any desired size, depending on the hydrophobicity desired and the hydrophilicity of the polyol moiety. A preferred range of alkyl chains is from 4 to 24 carbon atoms. An aryl group can consist of, e.g., a phenyl group, a naphthyl group, an anthracene group, a phenanthrene group, or a flavonoid group. An aralkyl group can consist of, e.g., a benzyl group, a tolyl group, a p-isooctylphenyl group, a 2-methylazulene group or a methylumbelliferyl group. A steroid group can be chosen from, for example, sapogenin estradiol, cholesterol or cortisol.

The hydrophilic polyol can be, for example, a monosaccharide, a disaccharide, an oligosaccharide, a sugar alcohol, a polyoxyethylene, or a polyoxyethylene sorbitan.

For compositions in which the hydrophilic polyol is a saccharide, the saccharide can be chosen from any currently commercially available saccharide species or can be synthesized. The saccharide can be a monosaccharide, a disaccharide, an oligosaccharide or a polysaccharide, or a combination thereof to form a saccharide chain. Some examples of the many possible saccharides to use include maltose, glucose, isomaltose, cellobiose, lactose, trehalose, maltotriose, sucrose, xylose, galactose, ribose, arabinose and mannose. Additionally, various oxygen atoms within the compounds can be substituted for by sulfur in order to decrease susceptibility to rapid hydrolytic cleavage by glycohydrolases in the body, such as $\alpha$- and $\beta$-glucosidase and amylase, and thus increase the therapeutic effect of these compounds. For example, the heteroatom of the sugar ring can be either oxygen or sulfur, or the linkage between monosaccharides in an oligosaccharide can be oxygen or sulfur. (Horton, D. and Wander, J. D., "Thio Sugars and Derivatives," *The Carbohydrates: Chemistry and Biochemistry*, 2d. Ed. Vol. IB, (W. Reyman and D. Horton eds.), pp. 799–842, (Academic Press, N.Y.), (1972)). Monosaccharide portions can have either dextrorotatory (D) or levorotatory (L) configuration. Oligosaccharides can have either $\alpha$ (alpha) or $\beta$ (beta) anomeric configuration.

Many alkyl glycosides can be synthesized by known procedures, i.e., chemically, as described, e.g., in Rosevear et al., *Biochemistry* 19:4108–4115 (1980) or Koeltzow and Urfer, *J. Am. Oil Chem. Soc.*, 61: 1651–1655 (1984), U.S. Pat. Nos. 3,219,656 and 3,839,318 or enzymatically, as described, e.g., in Li et al., *J. Biol. Chem.*, 266:10723–10726 (1991) or Gopalan et al., *J. Biol. Chem.* 267:9629–9638 (1992).

The linkage between the hydrophobic organic group and the hydrophilic polyol can include, among other possibilities, a glycosidic, thioglycosidic (Horton), amide (*Carbohydrates as Organic Raw Materials*, F. W. Lichtenthaler ed., VCH Publishers, New York, 1991) or ester linkage (*Sugar Esters: Preparation and Application*, J. C. Colbert ed., (Noyes Data Corp., New Jersey), (1974)). For saccharide polyol compositions, the linkage anomeric configuration of the sugar attachment can be either $\alpha$ (alpha) or $\beta$ (beta).

Examples from which useful surfactants can be chosen for the therapeutic composition include:
(1) saccharides joined with organic groupings:
(a) a saccharide joined with an alkyl group: alkyl glycosides, such as octyl-, nonyl-, decyl-, undecyl-, dodecyl-, tridecyl-, tetradecyl, pentadecyl-, and octadecyl $\alpha$- or $\beta$-D-maltoside, -glucoside or -sucroside (synthesized according to *Koeltzow and Urfer*; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-$\beta$-D-thiomaltoside (synthesized according to Defaye, J. and Pederson, C., "Hydrogen Fluoride, Solvent and Reagent for Carbohydrate Conversion Technology" in *Carbohydrates as Organic Raw Materials*, 247–265 (F. W. Lichtenthaler, ed.) VCH Publishers, New York (1991)); alkyl thioglucosides, such as heptyl- or octyl 1-thio $\beta$-D-glucopyranoside (Anatrace, Inc., Maumee, Ohio; see Saito, S. and Tsuchiya, T. *Chem. Pharm. Bull.* 33:503–508 (1985)); alkyl maltotriosides and alkyl maltotetraosides (synthesized according to *Koeltzow and Urfer*); decanoyl-N-methylglucamide (MEGA10) (Anatrace, Inc.); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in *Carbohydrates as Organic Raw Materials*, 127–153); derivatives of isomaltamine linked by urea to an alkyl chain (synthesized according to Kunz); long chain aliphatic carbonic acid ureides of sucrose $\beta$-amino-alkyl ethers (synthesized according to Gruber and Greber, "Reactive Sucrose Derivatives" in *Carbohydrates as Raw Materials*, pp. 95–116); long chain aliphatic carbonic acid amides of sucrose $\beta$-amino-alkyl ethers (synthesized according to Austrian Patent 382,381 (1987), *Chem. Abstr.*, 108:114719 (1988) and *Gruber and Greber*, pp. 95-116);

(b) a saccharide joined with an aryl group: phenyl α, β-D-glucopyranoside (synthesized according to *Carbohydrates*, P. M. Collins ed., p. 414 (Chapman and Hall, London, 1987)); 1-naphthyl α, β-maltoside (synthesized according to Matsubara, S. J., *Biochem* (Tokyo), 49:226-231 (1961)); vacciniin (6-benzoyl-D-glucose) (isolated according to *The Merck Index 9th Edition*, Windholz, Budavari, Stroumtsus and Fertig, eds., p. 9562 (Merck and Co., Rahway, 1976)); phenyl sucrose (synthesized according to Hough, L., Application of the Chemistry of Sucrose in *Carbohydrates as Organic Raw Materials*, 33-55);

(c) a saccharide joined to an aralkyl group: 4-nonylumbelliferyl-α-glucoside (synthesized according to Bieberich, E. and Legler, G., *Biol. Chem. Hoppe-Seyler*, 370:809-817 (1989));

(d) a saccharide joined to a fatty acid group: trehalose-6-mycolate (isolated according to Haferburg, et al., *Extracellular Microbial Lipids as Biosurfactants in Advances in Biochemical Engineering Biotechnology*, A. Fiechter, ed., Vol. 33, 53-93 (Springer-Verlag, Berlin, 1986)); stearyl sucrose (manufactured by Mitsubishi Food Corp., Japan; derivatives synthesized according to Benson, F. R., Polyol Surfactants in *Nonionic Surfactants*, M. J. Schick, ed., pp. 247-299 (Marcel Dekker, NY, 1967) and references therein);

(e) a saccharide joined with other groups: 2-hydroxymethyazulene glucopyranoside (synthesized according to Daub, et al., "From Carbohydrates to Pigments: An Exercise in Molecular Material Science and Material Transformation" in *Carbohydrates as Organic Raw Materials*, 340-350; stevioside (Sigma Chemical Co., St. Louis, Mo.); steroid polyols, such as digitonin (Sigma Chemical Co.));

(2) polyoxyethylenes joined with an organic grouping, such as nonaethylene glycol octylphenyl ether, e.g., Triton X-100 or NP-40 (Pierce Chemical Co., Rockford, Ill.), heptaethylene glycol octylphenyl ether, e.g., Triton X-114 (Pierce Chemical Co.) and others (see Enyeart, C. R., "Polyoxyethylene Alkylphenols" in *Nonionic Surfactants*, M. J. Schick, ed., 44-85 (Marcel Dekker, NY, 1967). Synthesis of desired polyoxyethylene compounds can be prepared as described in Fine, R. D., *J. Am. Oil Chem. Soc.*, 35:542 (1958);

(3) alkyl polyoxyethylene sorbitans, such as polyoxyethylene 20 sorbitan monolaurate (Tween-20) (Bio-Rad, Richmond, Calif.; Calbiochem, San Diego, Calif.) and others (Benson, F. R., Polyol Surfactants in *Nonionic Surfactants*, pp. 247-299).

Some preferred surfactants include a maltose polyol linked by glycosidic linkage to an alkyl chain of 12, 13 or 14 carbon atoms, i.e., dodecyl maltoside, tridecyl maltoside and tetradecyl maltoside. These compositions are commercially available (Anatrace, Inc.), are nontoxic (see Weber and Benning, *J. Nutr.*, 14:247-254 (1984) for report that the orally administered alkyl glycosides tested therein are metabolized to nontoxic metabolites), and are effective in dosages of from 10-400 μM.

The above examples are illustrative of the types of surfactants to be used in the method claimed herein; the list is not exhaustive. Derivatives of the above compounds which fit the criteria of the claims should also be considered when choosing a surfactant. All of the compounds can be screened for efficacy following the methods taught in the examples.

The composition can comprise, in addition to the surfactant, compounds and/or compositions that will also aid in relief of the symptoms of cystic fibrosis, such as a cyclic AMP agonist, a calcium ion agonist, human DNase 1, a sodium channel blocker or a pancreatic enzyme supplement, in dosages useful for relief of the symptoms of cystic fibrosis, as known to those skilled in the art. Cyclic AMP agonists can include, for example, forskolin and isoproterenol. Calcium ion agonists can include ionomycin, A23187, carbachol, bradykinin, duramycin and thapsigargin, for example. Sodium channel blockers can include amiloride and triamterene. Dosages for the above-mentioned additional compounds are established and known to those skilled in the art (see, e.g., Knowles et al., *N. Eng. J. Med.* 322:1189-1194 (1990)). Human DNase 1 can be prepared and administered according to Aitken et al., *Am. Rev. Res. Dis.*, 143:A298 (1991) and such preparation can include a permeability enhancing amount of a suitable surfactant as described herein. Pancreatic enzyme supplements are widely available commercially and can be administered in addition to a separate surfactant preparation or enzyme extracts (i.e., lipase, protease and/or amylase) can be combined with surfactants to create a combination preparation. Dosages of pancreatic enzyme supplements are known to those skilled in the art. Additionally, the composition can comprise the surfactant in liposome form, wherein the liposome contains an additional compound(s), as listed above.

In addition, another compound that can be administered in conjunction with the chosen surfactant is a nucleic acid encoding functional cystic fibrosis transmembrane conductance regulator protein or a biologically active portion thereof. The introduction of this nucleic acid to the body is preferably accomplished by complexing the nucleic acid with a liposome created from a suitable nonionic surfactant and delivering it to the lungs by aerosol inhalation (see, e.g., Hazinski et al., *Pediat. Pulmonol.* 9 Suppl., 5:122-123 (1990) and Nabel et al., *Science*, 249:1285-1288 (1990)). Liposome-mediated insertion and regulated expression of genes in the intact lungs of animals has been demonstrated using plasmids containing the gene complexed with cationic liposomes (Lipofectin, BRL, Inc.).

Additionally, cystic fibrosis transmembrane conductance regulator protein (CFTR) can be administered in conjunction with the chosen surfactant. CFTR can also be incorporated into liposomes for administration. CFFR compositions would preferably be administered either orally or directly to the lungs, for example, by aerosol inhalation. Aerosol administration of a protein to the lung has previously been accomplished in the case of α1-antitrypsin, an inhibitor of neutrophil elastase in lung (McElvaney et al., *Lancet*, 337:392-394 (1991)).

Compositions for treating cystic fibrosis are provided which comprise a suitable surfactant, as described above, and an agent selected from the group consisting of human DNase I, cystic fibrosis transmembrane conductance regulator protein or a biologically active portion thereof, nucleic acid encoding functional cystic fibrosis transmembrane conductance regulator protein, a cyclic AMP agonist, a calcium agonist, a sodium channel blocker and a pancreatic enzyme supplement, as also described above. More than one agent can be added to the surfactant. The ratio of surfactant to agent is dependent upon the dose desired of each individual compound.

The compositions may be administered orally, by inhalation, topically, endotracheally, parenterally (e.g., intravenously), by intramuscular injection, transdermally, or the like, although oral administration or inhalation is typically preferred. The amount of active compound administered will, of course, be dependent on the subject being treated, the subject's weight, the severity of symptoms, the manner of administration and the judgment of the prescribing physician. Generally, however, dosage will approximate that which is typical for the administration of compounds such as Exosurf Neonatal for the treatment or prevention of respiratory distress syndrome, as described in *Physicians' Desk Reference 47th Edition*, pp. 782–785 (Medical Economics Data, Montvale, N.J., 1993). Dosage optimally would be that required to achieve concentrations of 10–100 $\mu$M of alkylglycoside in extracellular fluid, e.g., respiratory surface after inhalation.

Depending on the intended mode of administration, the pharmaceutical compositions may be in the form of solid, semi-solid or liquid dosage forms, such as, for example, tablets, suppositories, pills, capsules, powders, liquids, suspensions, aerosols, liposomes, lotions, creams, gels, or the like, preferably in unit dosage form suitable for single administration of a precise dosage. The compositions, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, triethanolamine sodium acetate, triethanolamine oleate, etc. Actual methods of preparing such dosage forms are known, or will be apparent, to those skilled in this art; for example, see *Remington's Pharmaceutical Sciences*, E. W. Martin, (ed.), Mack Publishing Co., Easton, Pa.

Liposomes can be prepared according to Szoka and Papahadjopoulos, *Ann. Rev. Biophys. Bioeng.*, 9:467 (1980) and Kiwada et al., *Chem. Pharm. Bull.* 33:753 (1985). The surfactant liposome can be administered without an additional permeability enhancing compound or as a carrier for an additional permeability enhancing compound. Liposomes can be administered, for example, orally or by aerosol inhalation.

For oral administration, fine powders or granules may contain diluting or dispersing agents, and may be presented in water or in a syrup, in capsules or sachets in the dry state, or in a nonaqueous solution or suspension, wherein suspending agents may be included, in tablets wherein binders and lubricants may be included, or in a suspension in water or a syrup (see, e.g., Weber, N. and Benning, H. *J. Nutr.* 114:247–254 (1984)). Where desirable or necessary, flavoring, preserving, suspending, thickening, or emulsifying agents may be included. Tablets and granules may be coated.

For inhalation administration, the composition can be dissolved or dispersed in liquid form, such as in water or saline, preferably at a concentration at which the composition is fully solubilized and at which a suitable dose can be administered within an inhalable volume. A nebulizer (e.g. DeVilbiss 646) and compressed air generator (Pulmoaide, DeVilbiss) can be used to nebulize and deliver the composition to the airway surfaces. A suitable dose, for example, would place approximately 0.01–0.5 mmol per liter of the composition on the airway surfaces approximately 4 times per day. For infants, the dose may be in the range of approximately 80 $\mu$g/kg body weight. Delivery can be repeated several times a day, depending upon the specific dosage chosen and the rate at which the chosen composition is cleared from the airways, with the goal being to maintain $Cl^-$ permeability in the airway epithelial cells.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The exact amount of such compounds required will vary from subject to subject, depending on the species, age, and general condition of the subject, the severity of the disease that is being treated, the particular compound used, its mode of administration, and the like. Thus, it is not possible to specify an exact activity promoting amount. However, an appropriate amount may be determined by one of ordinary skill in the art using only routine testing given the teachings herein.

The recent development of an animal model for cystic fibrosis, mice homozygous for a disrupted CFTR gene that demonstrate many of the symptoms of human cystic fibrosis (Snouwaert et al., *Science*, 257:1083 (1992) and Clarke et al., *Science*, 257:1125 (1992), will allow the testing of surfactants in animals.

Any material added to the permeability enhancing compound should be pharmaceutically acceptable. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The present invention is more particularly described in the following examples which are intended as illustrative only since numerous modifications and variations therein will be apparent to those skilled in the art.

EXAMPLES $^{125}$I- Efflux Assay as a Measure of Cl-Permeability

T84 cells, a colonic adenocarcinoma line which expresses high amounts of the cystic fibrosis transmembrane conductance regulator (CFTR), which is the chloride channel defective in CF, show a stimulation of $^{125}$I- efflux (a measure of total cellular $Cl^-$ channel activity) when stimulated with forskolin (20 $\mu$M), an agonist which increases intracellular cAMP, or when stimulated with ionomycin (1 μM) an agonist which releases intracellular stores of Ca++. Forskolin or cAMP-stimulated Cl− channel activity is a standard measurement of the activity of Cl− channels represented by CFTR, while ionomycin or Ca++ ionophore-stimulated Cl− channel activity is a measure of the activity of Ca++-regulated Cl− channels which are different from those represented by CFTR. The CFTR Cl− channels are defective in CF, i.e., they do not open in response to forskolin or cAMP agonists; therefore $^{125}I$- efflux is not stimulated in CF cells by these agonists. In contrast Ca++-regulated Cl− channels operate normally in CF cells and are opened by ionomycin just as they are in T84 cells. NPPB, a blocker of some Cl− channels, inhibits $^{125}I$- efflux in T84 cells indicating that this assay is a measure of cellular Cl− channel activity.

The cells employed were (1) T84 cells (ATCC Accession No. CCL 248) (2) CFPAC-1 cells (ATCC Accession No. CRL 1918) (a newly established continuous line of pancreatic duct adenocarcinoma cells from a CF patient which is homozygous for the deletion of phenylalanine in the 508 position of CFTR, the mutation found in 70% of CF patients), (3) clones of CFPAC-1 cells which have been transduced with a retroviral vector (PLJ) containing (PLJ-CFTR-CFPAC) or lacking (PLJ-CFPAC) cDNA for functional CFTR, and (4) 2CFSMEo-, a continuous cell line derived from the tracheal submucosal gland of a CF patient whose exact genotype is unknown but which expresses the phenotype of defective Cl− channel permeability characteristic of CF.

In general, cells were washed with 1 ml of efflux medium (140 mM NaCl, 1 mM Ca gluconate, 1 mM Mg gluconate, 5 mM $KH_2PO_4$, 10 mM Tris-Hepes pH 7.4) four times and incubated with $^{125}I$- (3μl Na $^{125}I=12$ μC) in 1 ml of the same medium containing 5 mM D-glucose for 1 hour at 37° C. to load the cells with $^{125}I$. The cells were then washed quickly five times with 1 ml of the efflux medium at 22° C. to remove any $^{125}I$- that had not been taken up by the cells. One ml of the efflux medium at 22° C. was then added to initiate efflux and left in contact with the cells for 1 minute, before being removed and replaced with another 1 ml of medium. This replacement procedure was carried out 2-5 times before addition of the appropriate surfactant and/or agonist in 1 ml of the same medium to one culture dish (experimental) while to another dish 1 ml of medium without surfactant and/or agonist was added (control). Medium with or without surfactant and/or agonist was replaced at 0.5 minute intervals until the 10 minute time point when the replacement time was prolonged to 1 minute intervals. The samples of the replacement media were counted in a gamma counter to determine the amount of $^{125}I$- effluxing from the cells into the medium in each time interval. After 15 minutes when measurement of efflux was completed the cells were extracted for 30 minutes with 1 ml 0.2N NaOH, 0.15% SDS and the extract counted to determine the residual $^{125}I$- remaining in the cells.

The data is expressed as $^{125}I$- remaining in the cells (set at 100% at the initiation of efflux) and plotted against the time of efflux in minutes and/or as the ln % of $^{125}I$- remaining in the cells, plotted against the time of efflux in minutes. Expressing the data in the latter form facilitates calculation of the apparent rate constant for $^{125}I$- efflux using the equation $r=[\ln(R1)-\ln(R2)]/(t1-t2)$ where R1 and R2 are the percent of counts remaining in the cell layer at times t1 and t2 respectively.

Cell Viability Assays by Trypan Blue Exclusion

These experiments were carried out to evaluate the possible toxic effects of the alkylmaltosides on cell viability. T84 cells were incubated for 30 minutes in 1 ml of the same buffer in which the efflux studies were carried out containing 0.4% trypan blue in the absence or presence of 200 μM dodecylmaltoside (DM), 50 μM tri DM or 50 μM tetra DM (Anatrace, Inc., Maumee, Ohio). The cells were then examined in the light microscope for any changes in morphology and to determine uptake of the dye.

CFPAC-1 cells were released from the monolayer in the culture dish by incubation for 5 min. in 0.05% trypsin in phosphate-buffered saline (PBS). The cells were transferred into tubes and diluted 10-fold with PBS. An equal volume of PBS containing 0.8% trypan blue with or without 200 μM DM or 60 μM tri DM was then added and the suspension was incubated for 15 minutes at room temperature. The cells were then observed under the microscope for any morphological changes and the ratio of cells staining with trypan blue to those excluding the dye was determined.

Cellular Integrity Assay by LDH Leakage

The possible toxicity of DM to T84 cells was also determined by measuring the leakage of lactic dehydrogenase (LDH), a cytosolic enzyme into the culture medium after exposure of the cells to DM. Culture dishes containing T84 cells were washed with PBS three times and then incubated with 1 ml efflux medium containing 0, 10, 50, 100, 150, 200 and 500 μM DM for 1, 2, 5, 10 and 40 minutes at 22° C. LDH activity present in the medium was then determined by measuring the optical density of the solution at 340 nm after addition of NAD and lactic acid to the solution to measure the appearance of NADH. The amount of enzyme present was determined from standard curves of solutions containing 0-1.0 u/ml of enzyme. Total enzyme content of the cell monolayer was determined by lysing the cells and determining the LDH activity of the lysate. The results were then expressed as percent of total cellular LDH leaked into the medium plotted as a function of time of exposure to DM.

Alkyl Saccharides

DM shows a dose-dependent stimulation of $^{125}I$- efflux and therefore Cl− channel activity in T84 cells at concentrations from 10–400 μM. This effect could be due to stimulation of opening of cAMP-activated (CFTR) and/or Ca++-activated Cl− channels, both of which are found in this cell line. Alternatively DM may be stimulating $^{125}I$- efflux by intercalating in the plasma membrane of the cell and creating new ion channels which are permeable to $^{125}I$. It is also possible that all these mechanisms may be operative.

Other alkylmaltosides, i.e., tridecylmaltoside (tri DM) and tetradecylmaltoside (tetra DM) also produce a dose-dependent stimulation of $^{125}I$- efflux from T84 cells at concentrations from 10–100 μM. These alkylmaltosides appear to be more potent than DM since they show a greater stimulation of $^{125}I$- efflux at equimolar concentrations.

Other alkylsaccharides, i.e., dodecylsucrose (DS) and octylglucoside also stimulate $^{125}I$- efflux from T84 cells, but they are less potent than DM, tri DM and tetra DM.

DS at 100 μM shows a significantly smaller effect than DM at 100 μM. Octylglucoside shows an appreciable effect in stimulating $^{125}$I- efflux only at concentrations of 500 μM (0.5 mM) or greater, while dodecylglucoside (DG) at a concentration of 100 μM shows minimal effect. Therefore, both the length of the alkyl chain and the composition of the saccharide moiety can markedly affect the activity of the compounds in stimulating $^{125}$I- efflux and hence Cl$^-$ channel activity. Using DM as a reference standard, increasing the length of the alkyl chain by just one (tri DM) or two (tetra DM) carbon atoms markedly increases the potency of the compounds. Altering the composition of the saccharide moiety from maltose to sucrose in DS and from maltose to glucose in DG also markedly reduces the activity of the compounds as Cl$^-$ channel activators, particularly in the case of DG (which has one less glucose residue than DM), compared to DM at 100 μM. The hydrophobic (conferred by the alkyl chain)-hydrophilic (conferred by the saccharide moiety) balance of the molecule is approximately critical to its activity as a Cl$^-$ channel activator. Making the compound slightly more hydrophobic, as in going from DM to tri- and tetra-DM, increases the activity, but a more drastic shift to hydrophobicity as in going from DM to DG greatly reduces activity.

The effects of DM, tri DM and tetra DM in stimulating $^{125}$I- efflux from T84 cells are not due to lysis of the cells, because it is a graded and gradual response rather than the precipitous release that would be observed upon cell lysis, e.g., with sodium dodecyl sulfate (SDS). The response of DM is also reversible upon removal of the agent, indicating that channel activation and/or creation of new channels are not permanent. For example, addition of 100 μM or 200 μM DM to T84 cells preloaded with $^{125}$I- promptly initiates an increased rate of $^{125}$I- efflux from the cells compared to the control rate. This continues for 2 min., while the cells are continuously exposed to the agent, but as soon as the DM is removed the rate of $^{125}$I- efflux reverts to the control rate. Therefore, when DM is removed, the increased Cl$^-$ permeability returns to basal levels. In another experiment T84 cells which had been exposed to 100 μM or 200 μM DM for 10 minutes prior to the initiation of $^{125}$I- efflux showed similar rates of efflux to cells which had not been pre-exposed to DM. If DM remained in the medium during the efflux phase of the experiment, the rate of efflux was comparable to cells incubated in the same concentration of DM which had not been preincubated with DM. The results of these experiments support the contention that DM increases the plasma membrane permeability to Cl$^-$ only when it is present and that it produces no irreversible change in the Cl$^-$ permeability of the cells.

Additional evidence that DM produces an increase in Cl$^-$ permeability of the cell without impairing the normal cellular control of Cl$^-$ channel activity is indicated by the fact that T84 cells in which $^{125}$I- efflux has been stimulated by addition of 80–100 μM DM respond with an additional increase in the rate of $^{125}$I- efflux when exposed also to 20 μM forskolin in the presence of DM.

Tri DM and tetra DM, the most potent Cl$^-$ channel activators of the alkylmaltosides thus far tested, produced a dose-dependent increase in $^{125}$I- efflux in CFPAC-1 cells, a pancreatic adenocarcinoma cell line derived from a patient with CF that carries the mutation in CFTR which is present in about 70% of all CF patients. This cell line expresses the classic CF phenotype in that it is unresponsive to forskolin in the $^{125}$I- efflux assay while it responds briskly to ionomycin. This confirms that this cell line is functionally defective in cAMP-activated Cl$^-$ channels, i.e., CFTR, while retaining normally functional Ca$^{++}$-activated Cl$^-$ channels. Since the alkylmaltosides activate Cl$^-$ channel activity in CFPAC-1 cells, they are doing so by activating the defective CFTR channel if it is present in the cell membrane, activating Ca$^{++}$-mediated Cl$^-$ channels, or creating new channels through which Cl$^-$ can pass or a combination of all three.

DM, tri DM and tetra DM also stimulate Cl$^-$ channel activity as measured by increased $^{125}$I- efflux in CFPAC-1 cells which have been transduced with a retroviral vector lacking (PLJ-CFPAC-10) or containing (PLJ-CFTR-CFPAC-10) the cDNA for wild-type CFTR. The PLJ-transduced cells serve as a control for the PLJ-CFTR-transduced cells in which the CF Cl$^-$-channel defect has been corrected by introduction of functional CFTR. Therefore, the alkylmaltosides are effective in increasing the Cl$^-$ permeability of both CF and corrected pancreatic duct cells, demonstrating they would be effective therapeutic agents either used alone or in combination with gene or protein replacement therapy.

In addition to stimulating Cl$^-$ channel opening in pancreatic duct cells with both defective and functional CFTR, tri DM and tetra DM also show a dose-dependent stimulation of $^{125}$I- efflux in 2CFSMEo-, a human airway epithelial cell derived from tracheal submucosal gland of a patient with CF. This cell line is a compound heterozygote which carries the ΔF508 mutation on one allele and an unidentified mutation on the other allele. These cells have Cl$^-$ channels which can be blocked by NPPB. Therefore, the alkylmaltosides are effective in increasing the Cl$^-$ permeability of airway epithelial cells, the site of the principal morbidity which eventually leads to the death of CF patients.

The cellular toxicity of the alkylmaltosides was evaluated by trypan blue exclusion and leakage of the cytoplasmic enzyme lactic dehydrogenase (LDH) into the medium. Exposure of T84 cells to 200 μDM, 50 μM tri DM or 50 μM tetra DM for 30 minutes showed that these agents did not affect cellular morphology as assessed by light microscopic examination. No trypan blue staining of the cells was seen under these conditions. The ability of cells to exclude trypan blue is an index of cellular viability; dead or damaged cells take up the dye while intact cells exclude it. Similar results were seen when CFPAC-1 cells in suspension were exposed to 100 μM DM or 30 μM tri DM for 15 minutes. When T84 cells were exposed to concentrations of DM ranging from 10–500 μM and the medium assayed for LDH leakage from the cells, an index of cellular damage, little or no leakage of the enzyme was seen at concentrations up to 150 μM DM after up to 40 minutes of exposure. Concentrations of 200 μM or greater showed some leakage of the enzyme into the medium. Therefore, concentrations of DM below 150 μM appear to be non-toxic to cells.

Other Surfactants

Tween 20, which has the same 12 carbon alkyl side chain as DM, has some activity in the $^{125}$I- efflux assay, but is less potent than DM. Tween 80 which has a longer side chain with one double bond than Tween 20 (oleate vs. laurate) has less activity. Dimethylsulfoxide (DMSO), a well-known membrane permeabilizing agent, e.g., in skin, had no effect in stimulating $^{125}$I-efflux from T84 cells at a concentration of 17.6 mM, over 176 times the effective concentration of DM.

Triton X-100 stimulates $^{125}$I- efflux and therefore Cl$^-$ channel activity in T84 cells at a concentration of 100 μM. This is a representative of a surfactant class in which the polyol group is a polyoxyethylene, rather than a mono- or disaccharide as in the case of the glucosides, maltosides and sucrose derivatives, or a polyoxyethylene sorbitan, as in the case of the Tween group of surfactants, e.g., Tween 20, both of which we have also shown to have Cl$^-$-permeating activity.

Digitonin is a potent stimulator of $^{125}$I- efflux in T84 cells showing a pronounced effect at a concentration of 50 μM. Although it is unlikely that digitonin itself would have any practical use because of its toxicity, this experiment does indicate that surfactants with a steroidal hydrophobic moiety attached to an oligosaccharide also possess the ability to increase Cl$^-$ channel permeability in epithelial cells.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of increasing the permeability of epithelial cells to a chloride ion in a subject comprising administering a permeability enhancing amount of a composition comprising a nontoxic, nonionic surfactant having (1) a critical micelle concentration of less than about 10 mM and a hydrophile-lipophile balance number of from about 10 to 20, and (2) a suitable hydrophobic organic group joined by a linkage to a suitable hydrophilic polyol.

2. The method of claim 1, wherein the linkage is selected from the group consisting of a glycosidic linkage, a thioglycosidic linkage, an amide linkage, a ureide linkage and an ester linkage.

3. The method of claim 1, wherein the organic group is selected from the group consisting of alkyl, aralkyl, aryl and steroid.

4. The method of claim 1, wherein the polyol is a saccharide.

5. The method of claim 4, wherein the saccharide has a ring structure containing at least one sulfur atom.

6. The method of claim 4, wherein the monosaccharide residues of the saccharide are linked by a sulfur atom.

7. The method of claim 1, wherein the critical micelle concentration is less than about 1 mM and the hydrophile-lipophile balance number is from about 12 to about 14.

8. The method of claim 1, wherein the nonionic surfactant is an alkyl glycoside.

9. The method of claim 8, wherein the alkyl group of the alkyl glycoside has from four to twenty-four carbon atoms.

10. The method of claim 8, wherein the saccharide of the alkyl glycoside is maltose.

11. The method of claim 10, wherein the alkyl group has from twelve to fourteen carbon atoms.

12. The method of claim 1, wherein the composition further comprises a cyclic AMP agonist.

13. The method of claim 1, wherein the composition further comprises a calcium ion agonist.

14. The method of claim 1, wherein the composition further comprises human DNase 1.

15. The method of claim 1, wherein the composition further comprises a sodium channel blocker.

16. The method of claim 15, wherein the sodium channel blocker is amiloride.

17. The method of claim 1, wherein the composition further comprises a pancreatic enzyme supplement.

18. The method of claim 1, wherein the composition is administered by aerosol inhalation.

19. The method of claim 1, wherein the composition is administered orally.

20. The method of claim 1, wherein the nonionic surfactant is in liposome form and the liposome contains an additional permeability enhancing compound.

21. The method of claim 20, wherein the additional permeability increasing compound comprises a nucleic acid encoding functional cystic fibrosis transmembrane conductance regulator protein or a biologically active portion thereof.

22. The method of claim 20, wherein the additional permeability increasing compound comprises cystic fibrosis transmembrane conductance regulator protein or a biologically active portion thereof.

* * * * *

UNITED STATES PATENT AND TRADEMARK OFFICE
CERTIFICATE OF CORRECTION

PATENT NO. : 5,384,128
DATED : January 24, 1995
INVENTOR(S) : Elias Meezan, et al.

Figure 2:
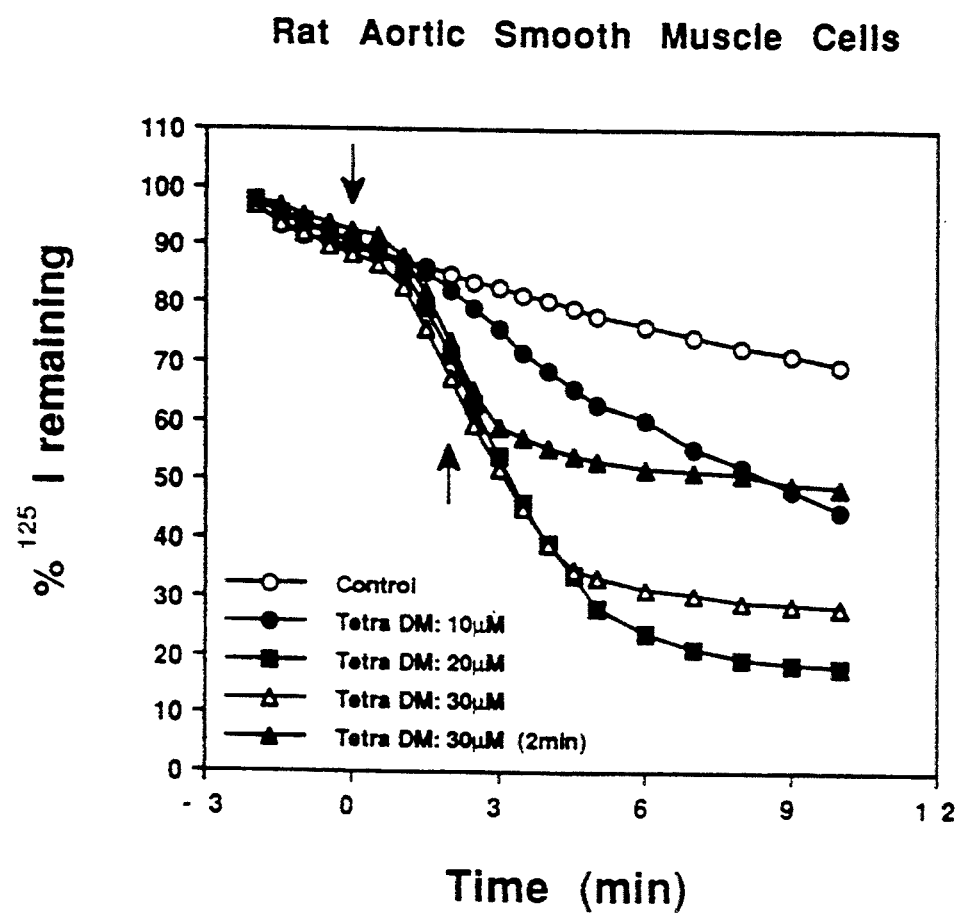
Figure 3:
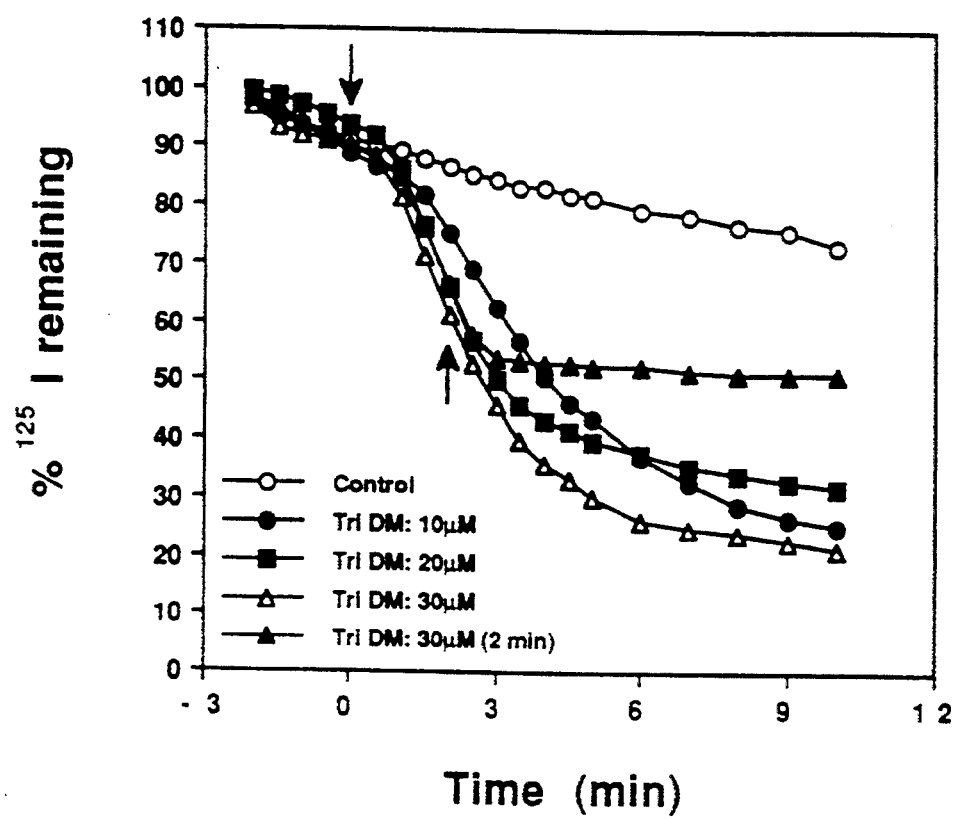
Figure 4:
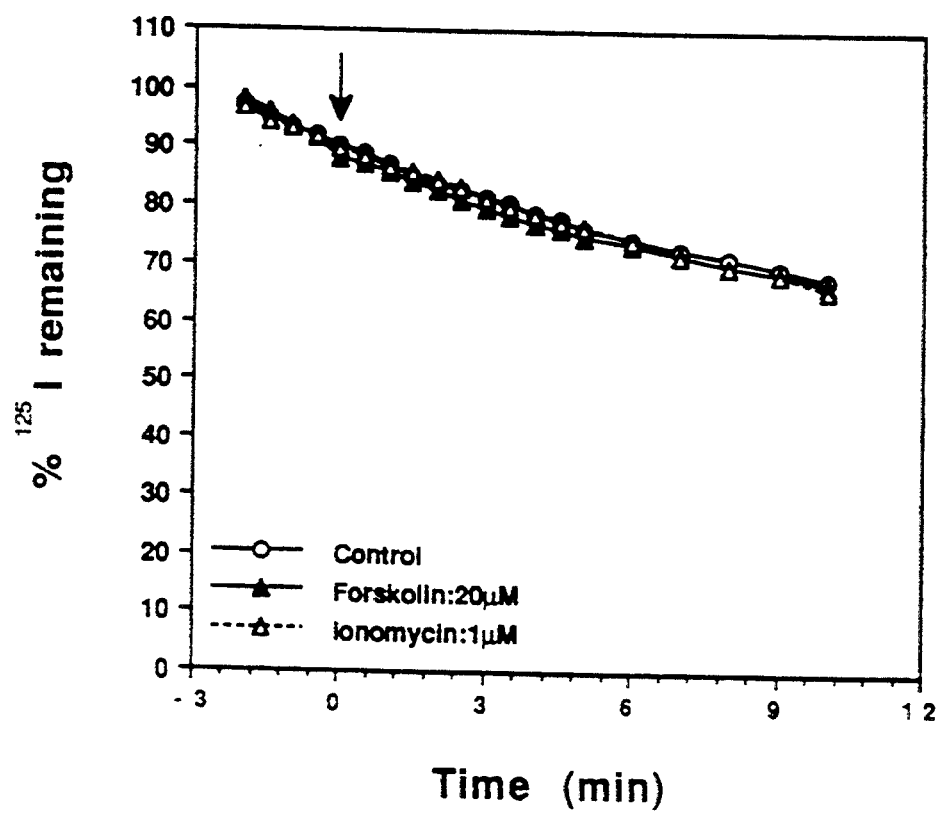
Figure 5:
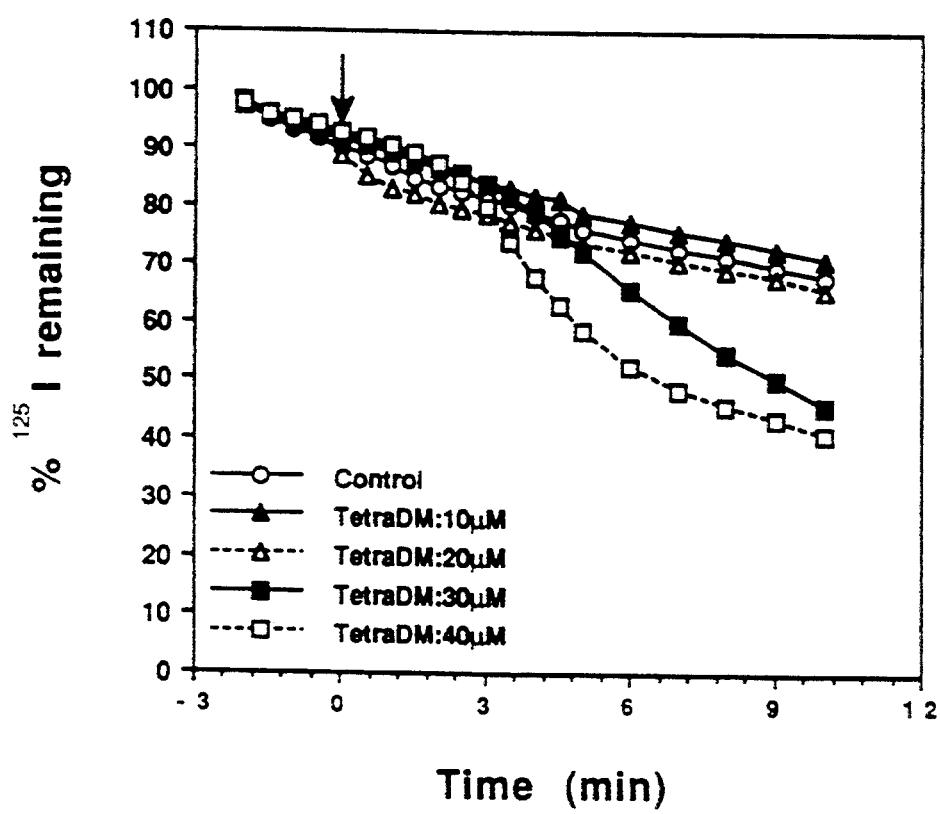
Figure 6:
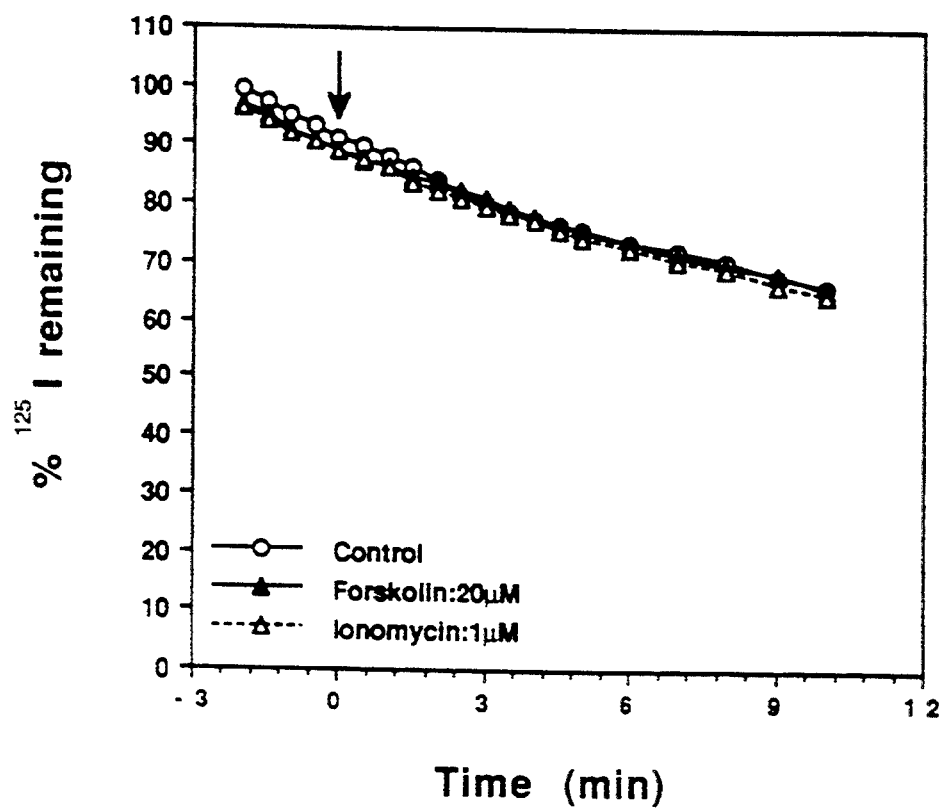
Figure 7:
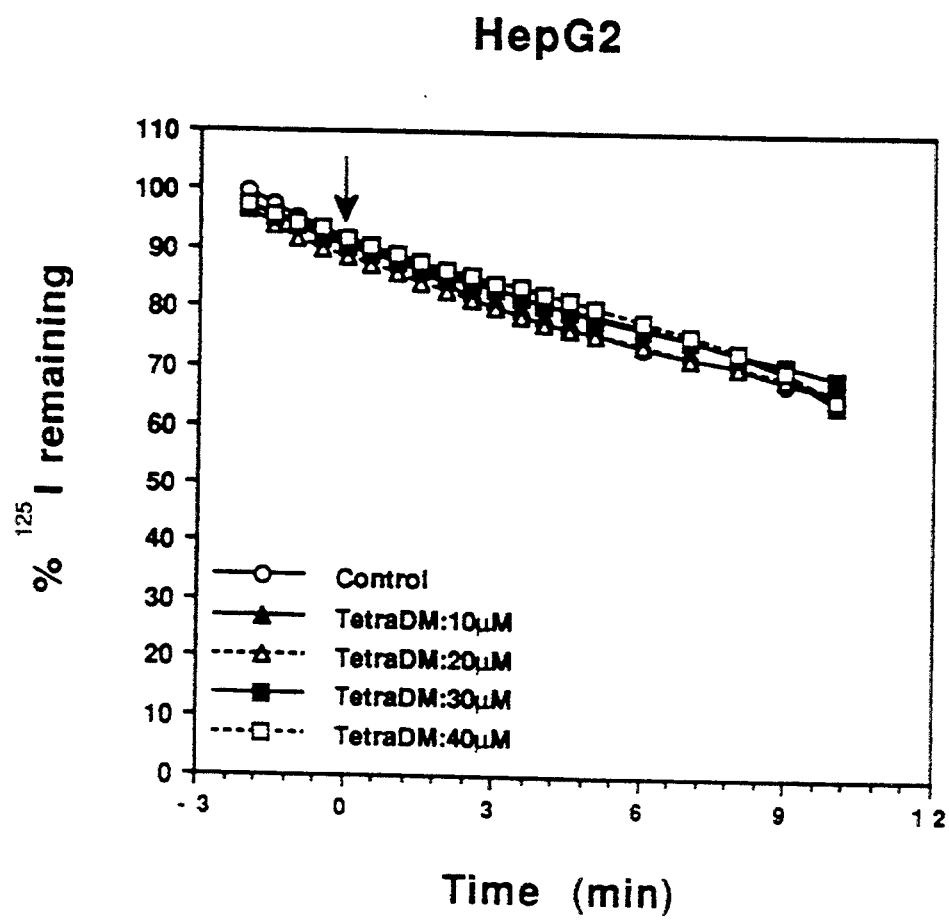
Figure 8:
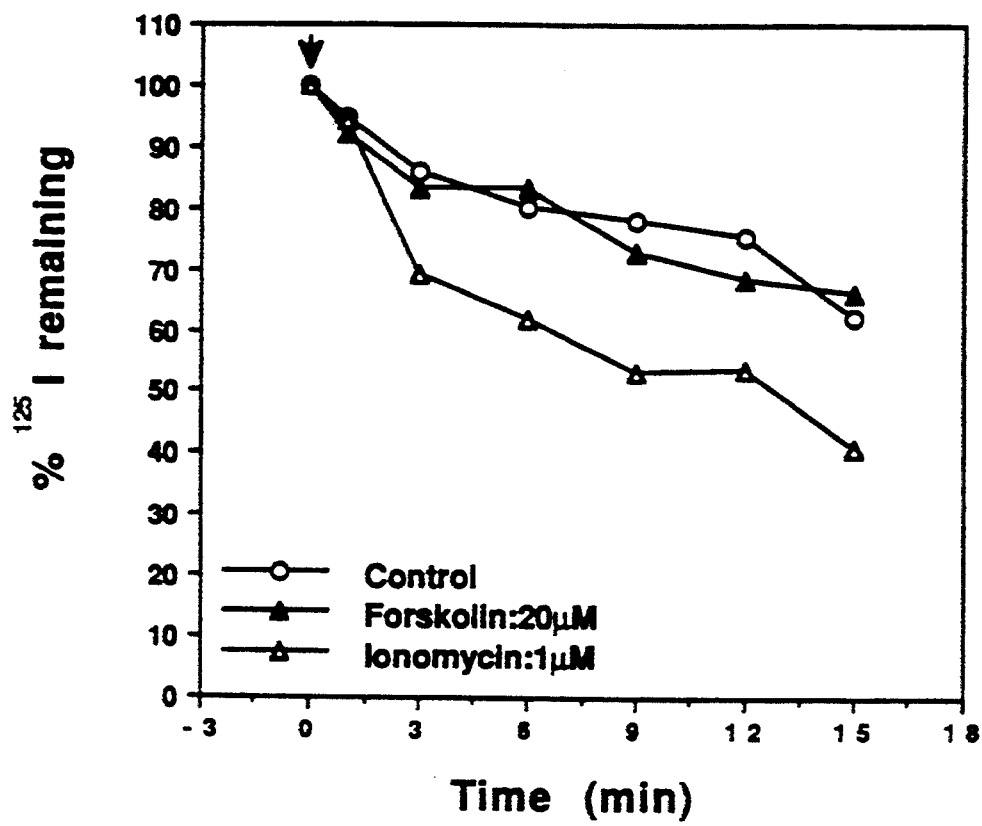
Figure 9:
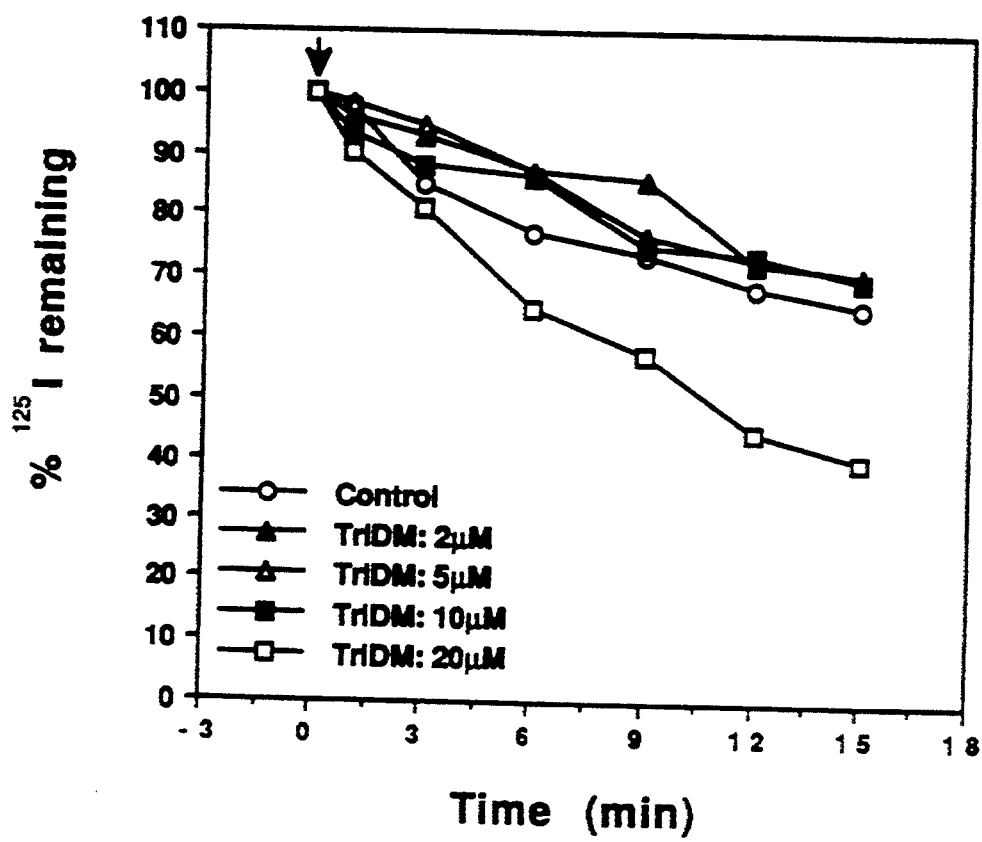
Figure 10:
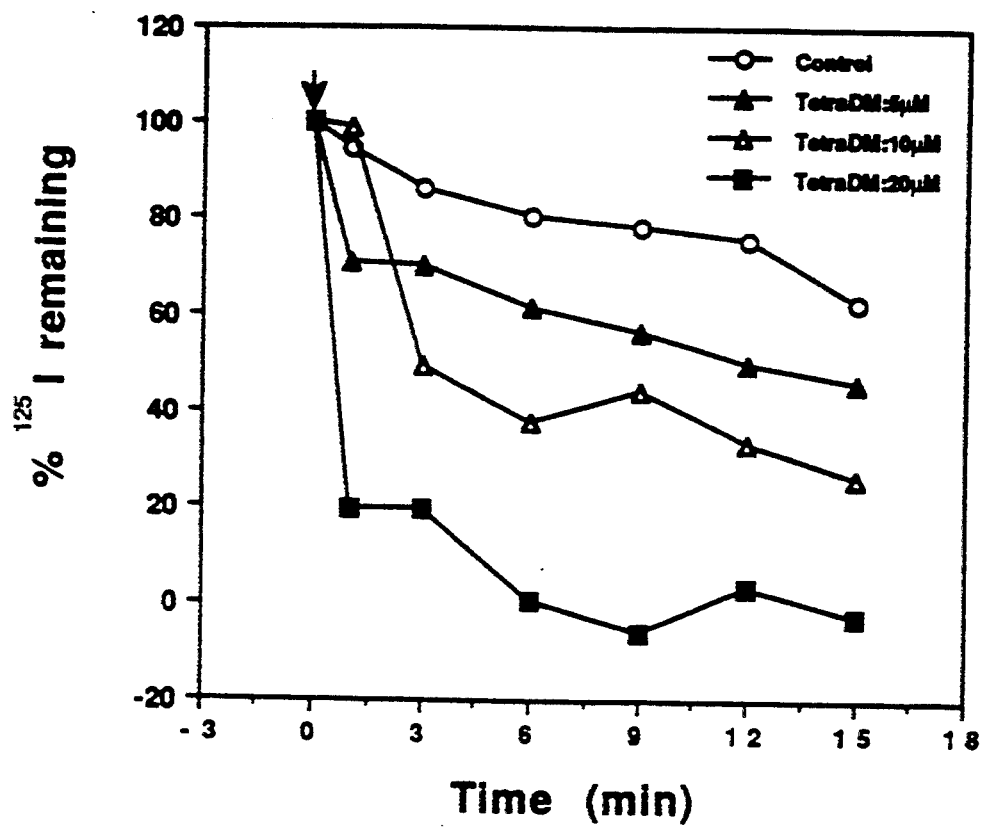

It is certified that error appears in the above-indentified patent and that said Letters Patent is hereby corrected as shown below:

```
Delete Figures 1-10.
Column 2, line 15, "Striver" should read --Scriver--.
Column 5, lines 36-37, "asteroid" should read --a steroid--.
Column 5, lines 46-47, "sapogenin estradiol" should read
     --sapogenin, estradiol--.
Column 7, line 33, "hydroxymethyazulene" should read
     --hydroxymethylazulene--.
Column 8, line 54, "CFFR" should read --CFTR--.
Column 11, line 8, "arc" should read --are--.
```

Signed and Sealed this

Sixth Day of June, 1995

BRUCE LEHMAN

Attest:

Attesting Officer

Commissioner of Patents and Trademarks